United States Patent
Scheid et al.

(10) Patent No.: US 9,471,057 B2
(45) Date of Patent: Oct. 18, 2016

(54) METHOD AND SYSTEM FOR POSITION CONTROL BASED ON AUTOMATED DEFECT DETECTION FEEDBACK

(75) Inventors: Paul Raymond Scheid, West Hartford, CT (US); Richard C. Grant, Ellington, CT (US); Alan Matthew Finn, Hebron, CT (US); Hongcheng Wang, Vernon, CT (US); Ziyou Xiong, Wethersfield, CT (US)

(73) Assignee: UNITED TECHNOLOGIES CORPORATION, Farmington, CT (US)

( * ) Notice: Subject to any disclaimer, the term of this patent is extended or adjusted under 35 U.S.C. 154(b) by 243 days.

(21) Appl. No.: 13/292,358

(22) Filed: Nov. 9, 2011

(65) Prior Publication Data

US 2013/0113915 A1    May 9, 2013

(51) Int. Cl.
*H04N 7/18* (2006.01)
*G05B 19/418* (2006.01)
*G01N 21/88* (2006.01)
(Continued)

(52) U.S. Cl.
CPC ......... *G05B 19/41875* (2013.01); *F01D 17/02* (2013.01); *F01D 21/003* (2013.01); *G01N 21/8851* (2013.01); *G01N 2021/8867* (2013.01); *G01N 2021/8893* (2013.01);
(Continued)

(58) Field of Classification Search
CPC .......... G01N 21/954; G01N 21/8803; G01N 2021/8867; G01N 2021/8893; G01N 21/8851; F03D 11/0091; H04N 2005/2255; H04N 7/183; F01D 17/02; F01D 21/003; G05B 19/41875; G05B 2219/37206; G05B 2219/37208; Y02P 90/22

USPC ........................................ 348/82, 92, E7.085
See application file for complete search history.

(56) References Cited

U.S. PATENT DOCUMENTS 5,070,401 A * 12/1991 Salvati et al. ................. 348/141
5,619,429 A *  4/1997 Aloni et al. ................... 700/279
(Continued)

FOREIGN PATENT DOCUMENTS

EP    1475629 A1    11/2004
EP    1609957 A2    12/2005
(Continued)

OTHER PUBLICATIONS

International Search Report of the International Searching Authority for International Application No. PCT/US2012/062652, May 28, 2013, 2 pages.
(Continued)

*Primary Examiner* — Christopher S Kelley
*Assistant Examiner* — Deirdre Beasley
(74) *Attorney, Agent, or Firm* — Cantor Colburn LLP

(57) ABSTRACT

A computer program product and method for performing position control on device members that have been identified as defective. The method may include providing a storage medium that stores data and programs used in processing images and a processing unit that processes the images, receiving, by the processing unit from an image capture device coupled to the processing unit, a set of images of a plurality of members inside of a device, detecting, by the processing unit, a defect in a first member of the plurality of members, and providing instructions to move the first member to an inspection position in the device. The device may be an engine and the members may be blades within the engine.

14 Claims, 3 Drawing Sheets

(51) Int. Cl.
*F01D 17/02* (2006.01)
*F01D 21/00* (2006.01)

(52) U.S. Cl.
CPC .............. *G05B 2219/37206* (2013.01); *G05B 2219/37208* (2013.01); *Y02P 90/22* (2015.11)

(56) References Cited

U.S. PATENT DOCUMENTS

| | | | |
|---|---|---|---|
| 5,741,965 A | | 4/1998 | Hernandez et al. |
| 5,774,212 A | * | 6/1998 | Corby, Jr. ................. 356/237.2 |
| 6,063,023 A | * | 5/2000 | Sakiyama .......... A61B 1/00193 600/117 |
| 6,153,889 A | * | 11/2000 | Jones ....................... 250/559.45 |
| 6,362,875 B1 | * | 3/2002 | Burkley .................... 356/139.03 |
| 6,424,733 B2 | * | 7/2002 | Langley ....................... 382/145 |
| 6,539,106 B1 | * | 3/2003 | Gallarda et al. .............. 382/149 |
| 7,064,811 B2 | * | 6/2006 | Twerdochlib ......... F01D 21/003 356/23 |
| 7,099,078 B2 | * | 8/2006 | Spencer ....................... 359/434 |
| 7,489,811 B2 | * | 2/2009 | Brummel et al. ............. 382/152 |
| 7,518,632 B2 | | 4/2009 | Konomura |
| 7,564,626 B2 | * | 7/2009 | Bendall et al. ............... 359/462 |
| 7,574,035 B2 | * | 8/2009 | Koonankeil ........... F01D 5/005 348/86 |
| 7,619,728 B2 | * | 11/2009 | Ogburn et al. ............ 356/237.1 |
| 7,656,445 B2 | * | 2/2010 | Heyworth ..................... 348/265 |
| 7,758,495 B2 | * | 7/2010 | Pease et al. ................... 600/104 |
| 2002/0128790 A1 | * | 9/2002 | Woodmansee .................. 702/81 |
| 2003/0063270 A1 | * | 4/2003 | Hunik ............................ 356/32 |
| 2004/0183900 A1 | * | 9/2004 | Karpen .............. G01N 21/8803 348/92 |
| 2004/0242961 A1 | | 12/2004 | Bughici |
| 2005/0016857 A1 | | 1/2005 | Kovarsky et al. |
| 2005/0129108 A1 | * | 6/2005 | Bendall et al. .......... 375/240.01 |
| 2006/0038988 A1 | * | 2/2006 | Thermos .............. G01N 21/954 356/241.1 |
| 2006/0050983 A1 | | 3/2006 | Bendall et al. |
| 2006/0078193 A1 | * | 4/2006 | Brummel ........... G01N 21/8806 382/152 |
| 2007/0132840 A1 | * | 6/2007 | Konomura ...................... 348/65 |
| 2008/0199304 A1 | * | 8/2008 | Moran .................. F01D 21/003 415/118 |
| 2009/0066939 A1 | * | 3/2009 | Venkatachalam et al. 356/237.1 |
| 2009/0201364 A1 | * | 8/2009 | Konomura ........... G01N 21/954 348/65 |
| 2009/0266160 A1 | * | 10/2009 | Jeffrey .................... F03D 1/008 73/455 |
| 2011/0013846 A1 | * | 1/2011 | Hori ............................. 382/218 |
| 2011/0025844 A1 | * | 2/2011 | Hori ...................... F01D 21/003 348/135 |
| 2011/0026805 A1 | * | 2/2011 | Hori ............................. 382/141 |
| 2011/0167633 A1 | * | 7/2011 | Anasis ................... F03D 1/003 29/889.1 |
| 2012/0121142 A1 | * | 5/2012 | Nagesh .............. G06K 9/00288 382/118 |
| 2012/0141251 A1 | * | 6/2012 | Moreno Benavides F04D 27/02 415/1 |
| 2013/0114879 A1 | * | 5/2013 | Scheid et al. ................. 382/145 |
| 2013/0207965 A1 | * | 8/2013 | Hori ............................. 345/419 |

FOREIGN PATENT DOCUMENTS

GB          2266354 A      10/1993
WO    WO 2010/020338 A1    2/2010

OTHER PUBLICATIONS

PCT International Preliminary Report on Patentability and Written Opinion of the International Searching Authority for International Application No. PCT/US2012/062652, May 13, 2014, 7 pages.
PCT International Search Report and the Written Opinion of the International Searching Authority, or the Declaration for International Application No. PCT/US2012/062652, May 28, 2013, 11 pages.

* cited by examiner

METHOD AND SYSTEM FOR POSITION CONTROL BASED ON AUTOMATED DEFECT DETECTION FEEDBACK

TECHNICAL FIELD OF THE DISCLOSURE

The present disclosure relates to position control used with automated defect inspection and, more particularly, relates to position control used with automated visual inspection of images or videos captured by borescopes.

BACKGROUND OF THE DISCLOSURE

Video inspection systems, such as borescopes, have been widely used for capturing images or videos of difficult-to-reach locations by "snaking" image sensor(s) to these locations. Applications utilizing borescope inspections include aircraft engine blade inspection, power turbine blade inspection, internal inspection of mechanical devices, and the like.

A variety of techniques for inspecting the images or videos provided by borescopes for determining defects therein have been proposed in the past. Most such techniques capture and display images or videos to human inspectors for defect detection and interpretation. Human inspectors then decide whether any defect within those images or videos exists. Other techniques utilize automated inspection techniques for analysis of images or video provided by a borescope.

Once defects are detected in a member of a device, the member must typically be manually located within the device and reinspected to confirm the presence and extent of the defect identified in the images or video. Identifying and locating the defective member within the device may be time-consuming and difficult because of the size of the device, the quantity of members within the device that may need to be sorted through, the location of the defective member within the device, and, in some cases, the similarity of each member to one another. Accordingly, it would be beneficial if an improved technique were developed for controlling the position of members, within a device, for which defects have been detected.

SUMMARY OF THE DISCLOSURE

In accordance with one aspect of the present disclosure, a method of performing position control is disclosed. The method may include providing a storage medium that stores data and programs used in processing images and a processing unit that processes the images, receiving, by the processing unit from an image capture device coupled to the processing unit, a set of images of a plurality of members inside of a device, detecting, by the processing unit, a defect in a first member of the plurality of members, and providing instructions to move the first member to an inspection position or other desired position in the device.

In accordance with another aspect of the present disclosure, a method for performing position control on defective blades in an aircraft engine is disclosed. The method may include providing a storage medium that stores data and programs used in processing video images and a processing unit that processes the video images, receiving from an image capture device video images of a plurality of the blades of the engine, the processing unit detecting a defect in the first blade of the plurality of blades based the video images, and providing instructions to move the first blade to an inspection position within the engine.

In accordance with yet another aspect of the present disclosure, a computer program product is disclosed. The computer program product may comprise a computer usable medium having a computer readable program code embodied therein. The computer readable program code may be adapted to be executed to implement a method for performing position control on defective blades in an aircraft engine. Such method may comprise receiving from an image capture device video images of a plurality of the blades of a stage of the engine, detecting a defect in the first blade of the plurality of blades based the video images, transmitting instructions to a turning tool rotate the first blade to an inspection position, and rotating the first blade to the inspection position.

While the present disclosure is susceptible to various modifications and alternative constructions, certain illustrative embodiments thereof, will be shown and described below in detail. It should be understood, however, that there is no intention to be limited to the specific embodiments disclosed, but on the contrary, the intention is to cover all modifications, alternative constructions, and equivalents falling within the spirit and scope of the present disclosure.

DETAILED DESCRIPTION OF THE DISCLOSURE

Figure 1:
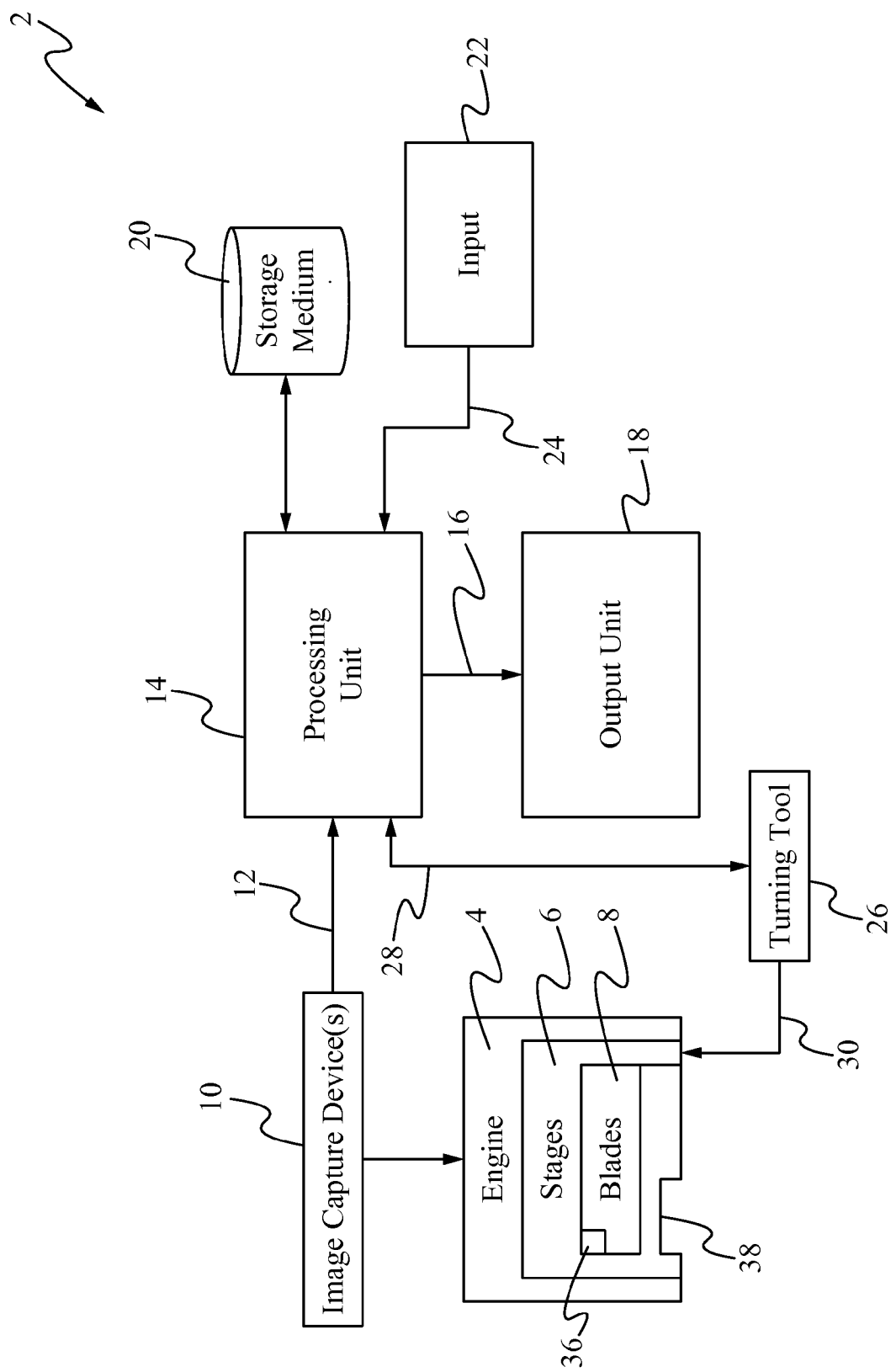
FIG. 1 is a schematic illustration of an embodiment of a defect detection and position control system, in accordance with the present disclosure.

Referring to FIG. 1, a schematic illustration of one embodiment of an automated defect detection and position control system 2 is shown. As shown, the system 2 may include an engine 4 having a plurality of stages 6, each of the stages having a plurality of blades 8, some or all of which may require visual inspection periodically or at predetermined intervals by an image capture device 10. In one embodiment, the image capture device 10 may be one or more borescopes. The engine 4 may be representative of a wide variety of engines, such as, jet aircraft engines, aeroderivative industrial gas turbines, steam turbines, diesel engines, automotive and truck engines, and the like. Notwithstanding the fact that the present disclosure has been described in relation to visual inspection of the blades 8 of an engine 4, in other embodiments, the system 2 may be employed to inspect other parts of the engine 4, as well as to perform inspection on the parts or members of other types of equipment and devices. Such parts/members are not limited to blades. For example, the system 2 may be used for medical endoscopes, inspecting critical interior surfaces in machined or cast parts, and the like.

Figure 3:
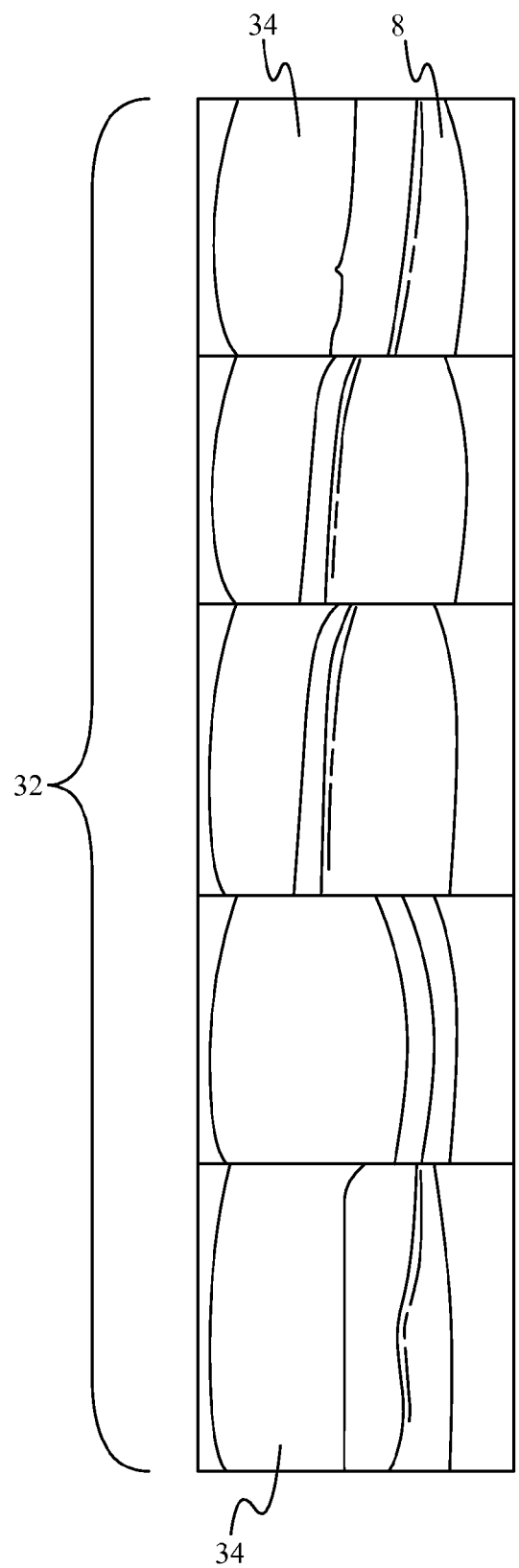
FIG. 3 illustrates an exemplary set of images received by the processing unit of FIG. 1.

The image capture device 10 may be an optical device having an optical lens or other imaging device or image sensor at one end and capable of capturing and transmitting images 34 or videos through a communication channel 12 to a processing unit 14. The image capture device 10 may be representative of any of a variety of flexible borescopes or fiberscopes, rigid borescopes, video borescopes or other devices, such as, endoscopes, which are capable of capturing and transmitting images 34 (FIG. 3) or videos of difficultto-reach areas through the communication channel 12. The communication channel 12 in turn may be an optical channel or alternatively, may be any other wired, wireless or radio channel or any other type of channel capable of transmitting images 34 and videos between two points including links involving the World Wide Web (www) or the internet.

With respect to the processing unit 14, it may be located on-site near or on the engine 4, or alternatively, it may be located at a remote site away from the engine 4. A storage medium 20 may be in communication with the processing unit 14. The storage medium 20 may store data and programs used in processing images 34 or videos of the blades 8, and monitoring and controlling the position of the blade(s) 8 in the engine 4. The processing unit 14 may receive and process images 34 of the blades 8 that are captured and transmitted by the image capture device 10 via the communication channel 12. Upon receiving the images 34, the processing unit 14 may automatically process the images 34 to perform feature extraction and image analysis and to determine whether there are any defects within any of the blades 8. In other embodiments the defect detection may be semi-automated.

The system 2 may include an output unit 18. Results (e.g., the defects) may be transmitted through communication channel 16 and displayed or printed by the output unit 18. The output unit may be a visual display, a printer, auditory unit, or the like. In addition, the output unit 18 may be a combination of the aforementioned exemplary output units. For example in one embodiment, the output unit may comprise a visual display, an auditory unit, and a printer. The results may include information regarding whether any defects in any of the blades 8 were found. Information about the type of defect, the location of the defect, size of the defect, etc. may also be reported as part of the results. For example, the output unit 18 may display a map of the engine 4 or a portion of the engine 4 and may identify the location of a defective blade 8 on the map. In another embodiment, the output unit 18 may display directions to guide a user to locate a defective blade 8 in the engine 4. The directions may be in a step by step format. In another embodiment, the output unit 18 may provide auditory directions or signals to guide a user to locate a defective blade 8 in the engine 4.

Similar to the communication channel 12, the communication channel 16 may be any of variety of communication links including, wired channels, optical or wireless channels, radio channels or possibly links involving the World Wide Web (www) or the internet. It will also be understood that although the output unit 18 has been shown as being a separate entity from the processing unit 14, this need not always be the case. Rather, in at least some embodiments, the output unit 18 may be part of the processing unit 14 and the results may be stored within and reported through the processing unit 14 as well. Furthermore, reporting of the results may involve storing the results in the storage medium 20 for future reference.

The system 2 may include an input unit 22 coupled to the processing unit 14. The input unit 22 may be a keyboard, touch screen or any other input device as known in the art. The input unit 22 may be coupled to the processing unit 14 by communication channel 24. Similar to the communication channel 12, communication channel 24 may be any of variety of communication links including, wired channels, optical or wireless channels, radio channels or possibly links involving the World Wide Web (www) or the internet.

The system may also include a turning tool 26 coupled to the processing unit 14 by communication channel 28. The turning tool 26 may be coupled to the engine 4 by direct mechanical coupling 30 or other means causing the movement of blades 8. In one embodiment the turning tool may be coupled to the engine stage 6. The turning tool 26 is configured to move the blades 8 of the engine 4 based on instructions provided to the turning tool 26 by the processing unit 14. In one embodiment, the turning tool 26 may be a motor configured to move a blade 8 of an engine stage 6 into an inspection position 38 based on instructions received from the processing unit 14. The inspection position 38 may, for example, be a port or appropriately sized opening in the engine 4 through which maintenance or other personnel may visually inspect the blade 8 directly or using a borescope. Similar to the communication channel 12, the communication channel 28 may be any of variety of communication links including, wired channels, optical or wireless channels, radio channels or possibly links involving the World Wide Web (www) or the internet.

Figure 2:
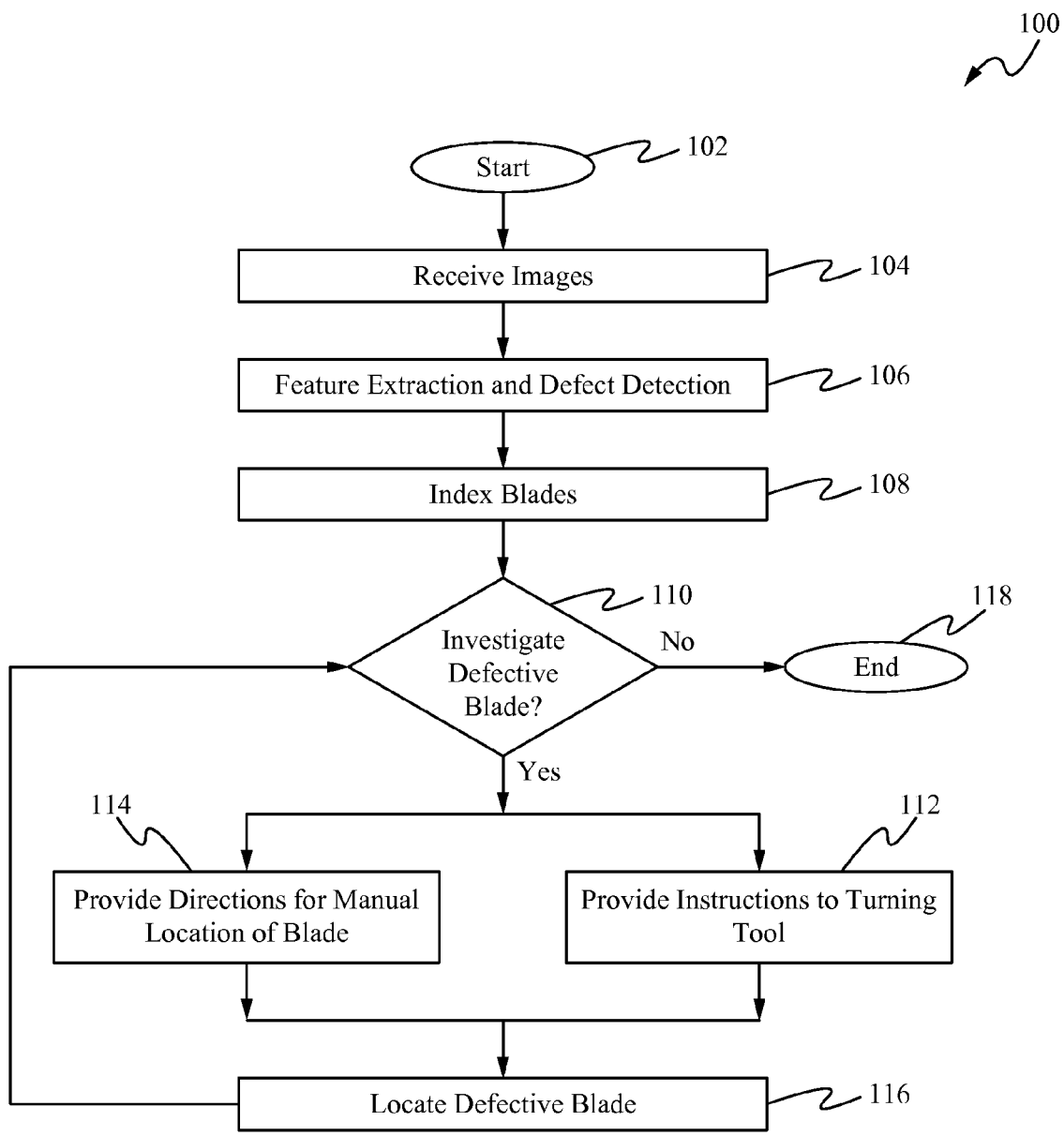
FIG. 2 is a flowchart illustrating exemplary steps of position control used in conjunction with automated defect detection, in accordance with the present disclosure.

FIG. 2 is an exemplary flowchart 100 showing sample steps which may be followed in performing automated defect detection and position control using the system 2. As shown, after starting at step 102, the process proceeds to step 104, in which an initial set 32 (see FIG. 3) of images 34 of members 8 of a device 4 may be received by the processing unit 14 from the image capture device 10. In one exemplary embodiment discussed below, the device may be an engine 4 and the members may be blades 8 within an engine stage 6. The images 34 may be video images 34 or frames, or the like. The set 32 of images 34 may be sequential in terms of the order in which they are captured by the image capture device (e.g. image one followed by image two, etc.). In other embodiments, the images 34 may be non-sequential with regard to the order in which the images 34 were captured by the image capture device 10. For example, every third image captured by the image capture device 10 may be received by the processing unit 14.

The blades 8 may be rotating in the engine 4 at the time the video images 34 are captured. For example, the blades 8 may rotate toward or away from the image capture device 10 when the images 34 are being captured. The images 34 captured may be of the same blade 8 in different positions in the field of view of the image capture device 10 and/or may be of a plurality of blades 8 in different positions in the field of view of the image capture device 10. Thus, there may be periodic or semi-periodic motion in the recorded videos of such inspected engine blades 8.

In step 106 the processing unit 14 may extract the features from each blade 8 from the set 32 of images 34 and may detect defects in one or more blades 8 of the engine 4. Various techniques of feature extraction and defect detection may be utilized by the processing unit 14. For example, defects may be determined by comparing received image data from the image capture device 10 with a normal model of an undamaged blade 8. The normal model may be created or otherwise learned automatically from data transmitted by the image capture device 10, or alternatively, the normal model may be created by input from a user.

In one embodiment, Robust Principal Component Analysis (RPCA) may be utilized to determine the normal model and/or detect defects. RPCA may be applied to the set 32 of images 34 to decompose the set 32 of images 34 received by the processing unit 14 from the image capture device 10 into a first series of low rank component images (low rank matrix) and a second series of sparse component anomaly images (sparse matrix). Typically blades 8 of an engine 4 are of the same size in a given engine stage 6. When a second blade 8 rotates to the same position as that which the first blade 8 had been in previously, the two images 34 taken at the two different instances are generally almost the same. The repetitive, nearly identical images 34 are captured in the low rank matrix and may be utilized to create a normal blade model. The damaged areas, for example nicks or dents, which tend to occupy a small percentage of the entire image, are captured in the sparse matrix and may, in some embodiments, be further processed for defect detection. An example of such additional processing done on image data in the sparse matrix may include statistical techniques such as polynomial fitting, blob extraction and size filtering, and morphological filtering and the like to detect non-smooth edges, to filter out small regions and sporadic pixels etc.

Alternatively, or in addition, a feature based approach for extracting features, such as, corner-like features and intensity gradient features, to determine any common features between images 34 may be utilized. In yet another alternative, an image based approach may be utilized where the entire image is used when comparing a current image with prior images 34. In other embodiments, a combination of feature based and image based approaches, or other commonly employed technique for aligning and comparing the current and the prior images 34 may be employed as well.

Techniques like SURF (Speeded Up Robust Features) and SIFT (Scale Invariant Feature Transform) may be employed for feature correspondence extraction or techniques, such as, FFT (Fast Fourier Transform) and NCC (Normalized Cross Co-relation) may be employed for image based comparison. All of the aforementioned techniques are well known in the art and, accordingly, for conciseness of expression, they have not been described here. Notwithstanding the fact that in the present embodiment, only the SURF, SIFT, FFT and NCC techniques for image comparison have been mentioned, in at least some embodiments, other types of techniques that are commonly employed for comparing images 34 or for detecting differences or defects in images 34 may be used.

The automated defect detection analysis performed by the processing unit 14 may also implement a classifier that confirms and verifies potential defects as either defects or non-defects. In at least some embodiments, the classifier may be implemented as a mathematical expression that may utilize the results of the automated analysis and may classify the results of the automated analysis into defects or non-defects and may report that classification as a binary output. Thus, for example, if the automated analysis technique used by the processing unit 14 finds a potential defect within the blades 8 corresponding to the set 32 of images 34 received, then the classifier may classify those results as a defect and may output a binary value of one (1). On the other hand, if the automated analysis did not find any defect, the classifier may classify those results as a non-defect and may output a binary value of zero (0).

The classifier may be implemented by the processing unit 14 in any of a variety of ways provided that the technique chosen is compatible with the automated analysis technique of the step 106. In at least some embodiments, the classifier may be a support vector machine classifier, while in other embodiments the classifier may be a neural net classifier, a bayesian classifier and the like. Classifiers other than those mentioned above may be employed in alternate embodiments.

Defects identified through automatic detection may include, but are not limited to, types of defects such as leading edge defects, erosions, nicks, dents, cracks or cuts, the location of the defects, the size of the defects and other defect parameters. After finding defects at step 106, the position of each blade 8 in the engine 4 or engine stage 6 is indexed. In one embodiment, a reference blade 36 is selected from the plurality of blades 8. The selection of the reference blade 36 may be done automatically by the processing unit 14 or may be selected by a user of the system 2 and input via the input unit 22 into the processing unit 14 for use in indexing. The position of reference blade 16 is retained in storage medium 20 during the subsequent movement of blades 8 by continuously counting subsequent blades 8 and their direction of motion as they are seen by the image capture device (10).

In one embodiment, a reference blade 36 is selected and the location of each blade 8 is indexed in the engine stage 6 according to its relative position to the reference blade 36. This relative position may be determined by the processing unit 14 by analysis of the set 32 of images 34 or video received from the image capture device 10 to determine the number of blades 8, away from the specific blade 8 to be indexed, is from the reference blade 36. In an embodiment, the relative position of the blade to be indexed from the reference blade 36 may be determined by analysis of the images 34 or video captured by the image capture device 10 while the blade 8 moves or rotates in the engine 4.

In another embodiment, the location of each blade 8 within the engine stage 6 may be indexed by each blade's 8 unique appearance. The processing unit 14 determines each blade's 8 unique appearance by analysis of the images 34 or video received from the image capture device 10. The processing unit 14 may utilize two dimensional segmented images 34 or three-dimensional images 34 synthesized from successive images 34 captured while the blade 8 moves or rotates in the engine 4. The unique appearance of a blade includes one or more of its visual appearance, 2D or 3D shape, defects (regardless of size or operational significance), color, etc.

In an alternative embodiment, where the blades 8 are highly similar, the blades 8 may be indexed by their offset from a reference blade 36 of unique appearance. Similar to above, the unique appearance of the reference blade 8 may be determined by the processing unit 14 in a variety of ways. For example, a blade 8 of unique appearance may be determined from two dimensional segmented images 34 or may be determined by three-dimensional images 34 synthesized from successive images 34 captured by the image capture device 10 while the blade 8 moves or rotates in the engine 4.

In step 110 the user may be provided with the option whether to investigate detected defects further. In some embodiments, the user may chose to dismiss further investigation, in which case the process to step 118 and ends. Alternatively, the user may chose to investigate the defects further.

If the user chooses to investigate the defects further, the process, in one embodiment, proceeds to step 112. In step 112, the processing unit 14 transmits to a turning tool 26 instructions to move the defective blade 8 to an inspection position 38. In some embodiments the turning tool 26 may be a motor. The turning tool 26 may be coupled, directly or indirectly, to the engine 4 or engine stage 6. The turning tool 26 may be configured to move or rotate the defective blade 8 from its current position to an inspection position 38 based on the instructions transmitted to the turning tool 26 by the processing unit 14.

After receiving the instructions from the processing unit 14, the turning tool 26 moves the defective blade 8 from its current position to the inspection position 38 where the blade 8 can undergo further inspection and analysis by a user.

Alternatively, the process may proceed from step 110 to step 114, where the processing unit 14 may provide to a user directions or guidance for locating the defective blade 8 in its current position and/or moving the defective blade 8 to an inspection position 38 without the assistance of the automated turning tool 26. The directions or guidance may be written, pictorial, auditory or a combination of some of all of the aforementioned. For example, in one embodiment the output unit 18 may display written directions advising a user to turn or rotate the engine stage a certain amount, to stop at a certain point, and the like. In another embodiment, the output unit 18 may display a map of the engine 4 and may identify on the map the location of the defective blade 8. In yet another embodiment, the processing unit 14 may provide auditory directions for locating and/or moving the defective blade 8 to an inspection position 38. Such auditory directions may include, but are not limited to, auditory spoken instructions, alarms, or beeps to guide the user.

Once a defective blade 8 is located and moved from its current position to the inspection position 38 in step 116, the process may proceed back to step 110 until all defective blades have been moved to an inspection position 38 for inspection or the user selects an option via the input unit 22 to discontinue or delay the inspection. At the point that there are no more defective blades 8 to inspect or the user selects to discontinue or delay inspection, the process ends at step 118.

INDUSTRIAL APPLICABILITY

In general, the present disclosure sets forth a computer program product and method for performing position control on device members identified as defective by an automated defect detection.

The method may include providing a storage medium that stores data and programs used in processing images and a processing unit that processes the images, receiving, by the processing unit from a image capture device coupled to the processing unit, a set of images of a plurality of members inside of a device, detecting, by the processing unit, a defect in a first member of the plurality of members, and providing instructions to move the first member to an inspection position in the device. The device may be an engine and the members may be blades within the engine.

The computer program product may comprise a computer usable medium having a computer readable program code embodied therein. The computer readable program code may be adapted to be executed to implement a method for performing position control on defective blades in an aircraft engine. Such method may comprise receiving from an image capture device video images of a plurality of the blades of a stage of the engine, detecting a defect in the first blade of the plurality of blades based the video images, transmitting instructions to a turning tool rotate the first blade to an inspection position, and rotating the first blade to the inspection position.

The present disclosure provides for indexing of and position control of device members identified as defective by automated defect detection, thereby more efficiently locating such defective members for follow-up manual inspection. Such indexing and position control allows potential problems or defects to be located, confirmed and resolved while minimizing the time and effort to do so.

While only certain embodiments have been set forth, alternatives and modifications will be apparent from the above description to those skilled in the art. These and other alternatives are considered equivalents and within the spirit and scope of this disclosure and the appended claims.

What is claimed is:

1. A method of performing position control, the method comprising:
   providing a storage medium that stores data and programs used in processing images and a processing unit that processes the images;
   receiving, by the processing unit from an image capture device coupled to the processing unit, a set of video images of a plurality of members in motion inside of a device;
   detecting, by the processing unit, a potential defect in a first member of the plurality of members by performing Robust Principal Component Analysis to simultaneously decompose the set of video images into a low rank matrix representing the first member and a sparse matrix representing the potential defect;
   implementing, by the processing unit, a classifier to confirm the potential defect is one of a defect or a non-defect;
   selecting, by the processing unit, a reference member from the plurality of members inside of the device;
   indexing a position of each of the plurality of members inside the device relative to the reference member;
   using the indexed positions of each of the plurality of members to locate the first member in a current position; and
   after the defect is detected and confirmed in the first member and the first member is located, providing instructions to move the first member having the defect from the current position to an inspection position in the device.

2. The method of claim 1, further comprising providing a turning tool coupled to the device and configured to move the plurality of members within the device, wherein the instructions are generated by the processing unit and transmitted to the turning tool.

3. The method of claim 1, further comprising providing a display coupled to the processing unit, wherein at least a portion of the instructions are displayed on the display.

4. The method of claim 1, further comprising providing an output unit coupled to the processing unit, wherein at least a portion of the instructions are auditory and are provided through the output unit.

5. The method of claim 1, further comprising providing a display coupled to the processing unit and displaying on the display the current location of the first member within the device.

6. The method of claim 1, wherein there is more than one image of each member in the set of images.

7. The method of claim 1, wherein the device is an engine and each member is a blade within a stage of the engine.

8. A method of performing position control on defective blades in an aircraft engine, the method comprising:
   providing a storage medium that stores data and programs used in processing video images and a processing unit that processes the video images;
   receiving from an image capture device video images of a plurality of the blades in motion inside of the engine;
   the processing unit detecting a potential defect in the first blade of the plurality of blades by performing Robust Principal Component Analysis to simultaneously decompose the video images into a low rank matrix representing the first blade and a sparse matrix representing the potential defect;

the processing unit implementing a classifier to confirm the potential defect is one of a defect or a non-defect;

the processing unit selecting a reference blade from the plurality of blades inside of the engine;

indexing a position of each of the plurality of the blades inside of the engine relative to the reference blade;

using the indexed positions of each of the plurality of the blades to locate the first blade in a current position; and after the defect is detected and confirmed in the first blade and the first blade is located, providing instructions to move the first blade having the defect from the current position to an inspection position within the engine.

9. The method of claim 8, further comprising providing a turning tool coupled to the engine and configured to move the plurality of blades within the engine, wherein the instructions provided are generated by the processing unit and transmitted to the turning tool.

10. The method of claim 9, wherein plurality of blades are disposed within a stage of the engine and the turning tool is a motor configured to rotate the blades.

11. The method of claim 8, wherein the reference blade has a unique feature.

12. The method of claim 8, further comprising indexing a location of each of the plurality of blades within the engine by each blade's appearance.

13. The method of claim 8, wherein there are at least three blades in the plurality of blades.

14. A computer program product, comprising a non-transitory computer readable medium having a computer readable program code stored on the non-transitory computer readable medium, the computer readable program code adapted to be executed to implement a method for performing position control on defective blades in an aircraft engine, the method comprising:

receiving from an image capture device video images of a plurality of the blades of a stage in motion inside of the engine;

detecting a potential defect in the first blade of the plurality of blades by performing Robust Principal Component Analysis to simultaneously decompose the video images into a low rank matrix representing the first blade and a sparse matrix representing the potential defect;

implementing a classifier to confirm the potential defect is one of a defect or a non-defect;

selecting a reference blade from the plurality of blades inside of the engine;

indexing a position of each of the plurality of the blades inside the engine relative to the reference blade;

using the indexed positions of each of the plurality of the blades to locate the first blade in a current position;

after the defect is detected and confirmed in the first blade and the first blade is located, transmitting instructions to a turning tool rotate the first blade having the defect from the current position to an inspection position; and rotating the first blade from the current position to the inspection position.

\* \* \* \* \*